United States Patent
Baldwin

(10) Patent No.: US 11,759,547 B2
(45) Date of Patent: Sep. 19, 2023

(54) POLYMERS

(71) Applicant: MicroVention, Inc., Aliso Viejo, CA (US)

(72) Inventor: Aaron Baldwin, Orange, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 141 days.

(21) Appl. No.: 17/499,755

(22) Filed: Oct. 12, 2021

(65) Prior Publication Data

US 2022/0105236 A1 Apr. 7, 2022

Related U.S. Application Data

(60) Continuation of application No. 16/838,730, filed on Apr. 2, 2020, now Pat. No. 11,179,492, which is a division of application No. 15/179,212, filed on Jun. 10, 2016, now Pat. No. 10,639,396.

(60) Provisional application No. 62/174,425, filed on Jun. 11, 2015.

(51) Int. Cl.
| | |
|---|---|
| A61L 24/06 | (2006.01) |
| A61L 31/14 | (2006.01) |
| A61L 24/00 | (2006.01) |
| A61L 31/18 | (2006.01) |

(52) U.S. Cl.
CPC .............. *A61L 24/06* (2013.01); *A61L 24/001* (2013.01); *A61L 24/0031* (2013.01); *A61L 31/14* (2013.01); *A61L 31/145* (2013.01); *A61L 31/18* (2013.01); *A61L 2430/36* (2013.01)

(58) Field of Classification Search
None
See application file for complete search history.

(56) References Cited

U.S. PATENT DOCUMENTS

| | | |
|---|---|---|
| 3,709,842 A | 1/1973 | Stoy et al. |
| 3,743,686 A | 7/1973 | Koch et al. |
| 3,749,085 A | 7/1973 | Wilson et al. |
| 4,020,829 A | 5/1977 | Wilson et al. |
| 4,301,803 A | 11/1981 | Handa et al. |
| 4,304,232 A | 12/1981 | Michaels |
| 4,365,621 A | 12/1982 | Brundin |
| 4,402,319 A | 9/1983 | Handa et al. |
| 4,493,329 A | 1/1985 | Crawford et al. |
| 4,509,504 A | 4/1985 | Brundin |
| 4,529,739 A | 7/1985 | Scott et al. |
| 4,551,132 A | 11/1985 | Pasztor et al. |

(Continued)

FOREIGN PATENT DOCUMENTS

| | | |
|---|---|---|
| CA | 2551373 C | 6/2014 |
| CN | 103251596 A | 8/2013 |

(Continued)

OTHER PUBLICATIONS

Ahuja et al., Platinum coil coatings to increase thrombogenicity: a preliminary study in rabbits, AJNR, 14: 794-789 (1993).

(Continued)

*Primary Examiner* — Peter A Salamon
(74) *Attorney, Agent, or Firm* — K&L Gates LLP; Brian J. Novak; Benjamin D. Heuberger

(57) ABSTRACT

Described herein are polymers and associated methods to occlude structures and malformations of the vasculature with polymers with delayed controlled rates of expansion. Methods of forming such devices are also disclosed.

21 Claims, 1 Drawing Sheet

Scheme 2

(56) References Cited

U.S. PATENT DOCUMENTS

| | | | |
|---|---|---|---|
| 4,663,358 | A | 5/1987 | Hyon et al. |
| 4,795,741 | A | 1/1989 | Leshchiner et al. |
| 4,819,637 | A | 4/1989 | Dormandy, Jr. et al. |
| 4,932,419 | A | 6/1990 | de Toledo |
| 4,951,677 | A | 8/1990 | Crowley et al. |
| 4,994,069 | A | 2/1991 | Ritchart et al. |
| 5,120,349 | A | 6/1992 | Stewart et al. |
| 5,122,136 | A | 6/1992 | Guglielmi et al. |
| 5,129,180 | A | 7/1992 | Stewart |
| 5,133,731 | A | 7/1992 | Butler et al. |
| 5,147,646 | A | 9/1992 | Graham |
| 5,154,705 | A | 10/1992 | Fleischhacker et al. |
| 5,163,952 | A | 11/1992 | Froix |
| 5,165,421 | A | 11/1992 | Fleischhacker et al. |
| 5,217,484 | A | 6/1993 | Marks |
| 5,226,911 | A | 7/1993 | Chee et al. |
| 5,258,042 | A | 11/1993 | Mehta |
| 5,304,194 | A | 4/1994 | Chee et al. |
| 5,312,415 | A | 5/1994 | Palermo |
| 5,350,397 | A | 9/1994 | Palermo et al. |
| 5,354,290 | A | 10/1994 | Gross |
| 5,373,619 | A | 12/1994 | Fleischhacker et al. |
| 5,382,259 | A | 1/1995 | Phelps et al. |
| 5,382,260 | A | 1/1995 | Dormandy, Jr. et al. |
| 5,443,478 | A | 8/1995 | Purdy |
| 5,447,727 | A | 9/1995 | Graham |
| 5,449,369 | A | 9/1995 | Imran |
| 5,456,693 | A | 10/1995 | Conston et al. |
| 5,469,867 | A | 11/1995 | Schmitt |
| 5,476,472 | A | 12/1995 | Dormandy, Jr. et al. |
| 5,483,022 | A | 1/1996 | Mar |
| 5,508,342 | A | 4/1996 | Antonucci |
| 5,522,822 | A | 6/1996 | Phelps et al. |
| 5,525,334 | A | 6/1996 | Ito et al. |
| 5,536,274 | A | 7/1996 | Neuss |
| 5,538,512 | A | 7/1996 | Zenzen |
| 5,539,071 | A | 7/1996 | Staffler |
| 5,541,234 | A | 7/1996 | Unger et al. |
| 5,549,624 | A | 8/1996 | Mirigian |
| 5,567,435 | A | 10/1996 | Hubbell et al. |
| 5,573,520 | A | 11/1996 | Schwartz et al. |
| 5,573,994 | A | 11/1996 | Kabra et al. |
| 5,578,074 | A | 11/1996 | Mirigian |
| 5,580,568 | A | 12/1996 | Greff et al. |
| 5,582,610 | A | 12/1996 | Grossi et al. |
| 5,582,619 | A | 12/1996 | Ken |
| 5,603,991 | A | 2/1997 | Kupiecki et al. |
| 5,607,417 | A | 3/1997 | Batich et al. |
| 5,609,629 | A | 3/1997 | Fearnot et al. |
| 5,612,050 | A | 3/1997 | Rowe et al. |
| 5,624,461 | A | 4/1997 | Mariant |
| 5,624,685 | A | 4/1997 | Takahashi et al. |
| 5,634,936 | A | 6/1997 | Linden et al. |
| 5,645,558 | A | 7/1997 | Horton |
| 5,651,979 | A | 7/1997 | Ron et al. |
| 5,658,308 | A | 8/1997 | Snyder |
| 5,667,767 | A | 9/1997 | Greff et al. |
| 5,672,634 | A | 9/1997 | Tseng et al. |
| 5,677,067 | A | 10/1997 | Kojima |
| 5,678,296 | A | 10/1997 | Fleischhacker et al. |
| 5,690,666 | A | 11/1997 | Berenstein et al. |
| 5,690,667 | A | 11/1997 | Gia |
| 5,690,671 | A | 11/1997 | McGurk et al. |
| 5,695,480 | A | 12/1997 | Evans et al. |
| 5,702,361 | A | 12/1997 | Evans et al. |
| 5,718,711 | A | 2/1998 | Berenstein et al. |
| 5,725,568 | A | 3/1998 | Hastings |
| 5,749,894 | A | 5/1998 | Engelson |
| 5,750,585 | A | 5/1998 | Park et al. |
| 5,752,974 | A | 5/1998 | Rhee et al. |
| 5,755,658 | A | 5/1998 | Wallace et al. |
| 5,766,160 | A | 6/1998 | Samson et al. |
| 5,766,219 | A | 6/1998 | Horton |
| 5,823,198 | A | 10/1998 | Jones et al. |
| 5,827,231 | A | 10/1998 | Harada |
| 5,830,178 | A | 11/1998 | Jones et al. |
| 5,834,118 | A | 11/1998 | Rangnby |
| 5,843,743 | A | 12/1998 | Hubbell et al. |
| 5,851,508 | A | 12/1998 | Greff et al. |
| 5,853,418 | A | 12/1998 | Ken |
| 5,853,419 | A | 12/1998 | Ken et al. |
| 5,863,551 | A | 1/1999 | Woerly |
| 5,883,705 | A | 3/1999 | Minne et al. |
| 5,891,155 | A | 4/1999 | Irie |
| 5,952,232 | A | 9/1999 | Rothman |
| 5,976,162 | A | 11/1999 | Doan et al. |
| 5,980,514 | A | 11/1999 | Kupiecki et al. |
| 6,004,338 | A | 12/1999 | Ken et al. |
| 6,004,573 | A | 12/1999 | Rathi et al. |
| 6,013,084 | A | 1/2000 | Ken et al. |
| 6,015,424 | A | 1/2000 | Rosenbluth et al. |
| 6,017,977 | A | 1/2000 | Evans et al. |
| 6,051,607 | A | 4/2000 | Greff |
| 6,063,100 | A | 5/2000 | Diaz et al. |
| 6,066,149 | A | 5/2000 | Samson et al. |
| 6,093,199 | A | 7/2000 | Brown et al. |
| 6,096,034 | A | 8/2000 | Kupiecki et al. |
| 6,103,865 | A | 8/2000 | Bae et al. |
| 6,136,015 | A | 10/2000 | Kurz et al. |
| 6,146,373 | A | 11/2000 | Cragg et al. |
| 6,159,165 | A | 12/2000 | Ferrera et al. |
| 6,168,570 | B1 | 1/2001 | Ferrera |
| 6,171,326 | B1 | 1/2001 | Ferrera et al. |
| 6,179,857 | B1 | 1/2001 | Diaz et al. |
| 6,187,024 | B1 | 2/2001 | Boock et al. |
| 6,193,728 | B1 | 2/2001 | Ken et al. |
| 6,201,065 | B1 | 3/2001 | Pathak et al. |
| 6,224,893 | B1 | 5/2001 | Langer |
| 6,231,590 | B1 | 5/2001 | Slaikeu et al. |
| 6,238,403 | B1 | 5/2001 | Greene, Jr. et al. |
| 6,245,090 | B1 | 6/2001 | Gilson et al. |
| 6,270,748 | B1 | 8/2001 | Annan et al. |
| 6,280,457 | B1 | 8/2001 | Wallace et al. |
| 6,281,263 | B1 | 8/2001 | Evans et al. |
| 6,287,318 | B1 | 9/2001 | Villar et al. |
| 6,299,604 | B1 | 10/2001 | Ragheb et al. |
| 6,299,619 | B1 | 10/2001 | Greene, Jr. et al. |
| 6,299,627 | B1 | 10/2001 | Eder et al. |
| 6,303,100 | B1 | 10/2001 | Ricci et al. |
| 6,312,421 | B1 | 11/2001 | Boock |
| 6,333,020 | B1 | 12/2001 | Wallace et al. |
| 6,335,384 | B1 | 1/2002 | Evans et al. |
| 6,342,202 | B1 | 1/2002 | Evans et al. |
| 6,342,541 | B1 | 1/2002 | Lombradi |
| 6,375,880 | B1 | 4/2002 | Cooper |
| 6,399,886 | B1 | 6/2002 | Avellanet |
| 6,423,085 | B1 | 7/2002 | Murayama et al. |
| 6,425,893 | B1 | 7/2002 | Guglielmi et al. |
| 6,454,738 | B1 | 9/2002 | Tran et al. |
| 6,503,244 | B2 | 1/2003 | Hayman |
| 6,511,468 | B1 | 1/2003 | Cragg et al. |
| 6,511,472 | B1 | 1/2003 | Hayman et al. |
| 6,531,111 | B1 | 3/2003 | Whalen et al. |
| 6,537,569 | B2 | 3/2003 | Cruise et al. |
| 6,558,367 | B1 | 5/2003 | Cragg et al. |
| 6,565,551 | B1 | 5/2003 | Jones et al. |
| 6,569,190 | B2 | 5/2003 | Whalen et al. |
| 6,599,448 | B1 | 7/2003 | Ehrhard, Jr. et al. |
| 6,602,261 | B2 | 8/2003 | Greene, Jr. et al. |
| 6,605,294 | B2 | 8/2003 | Sawhney |
| 6,623,450 | B1 | 9/2003 | Dutta |
| 6,634,361 | B1 | 10/2003 | Nikolchev et al. |
| 6,645,167 | B1 | 11/2003 | Whalen et al. |
| 6,684,884 | B2 | 2/2004 | Nikolchev et al. |
| 6,699,222 | B1 | 3/2004 | Jones et al. |
| 6,723,108 | B1 | 4/2004 | Jones et al. |
| 6,756,031 | B2 | 6/2004 | Evans et al. |
| 6,759,028 | B2 | 7/2004 | Wallace et al. |
| 6,849,081 | B2 | 2/2005 | Sepetka et al. |
| 6,860,893 | B2 | 3/2005 | Wallace et al. |
| 6,878,384 | B2 | 4/2005 | Cruise et al. |
| 6,887,974 | B2 | 5/2005 | Pathak et al. |
| 6,962,689 | B2 | 11/2005 | Whalen et al. |
| 6,964,657 | B2 | 11/2005 | Cragg et al. |

(56) References Cited

U.S. PATENT DOCUMENTS

| | | |
|---|---|---|
| 7,018,365 B2 | 3/2006 | Strauss et al. |
| 7,033,374 B2 | 4/2006 | Schaefer et al. |
| 7,066,904 B2 | 6/2006 | Rosenthal et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,422,569 B2 | 9/2008 | Wilson et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,625,580 B1 | 12/2009 | Langer |
| 7,695,484 B2 | 4/2010 | Wallace et al. |
| 7,815,835 B2 | 10/2010 | Stampfl |
| 7,976,527 B2 | 7/2011 | Cragg et al. |
| 7,988,992 B2 | 8/2011 | Omidian et al. |
| 8,066,667 B2 | 11/2011 | Hayman et al. |
| 8,172,862 B2 | 5/2012 | Wallace et al. |
| 8,183,229 B2 | 5/2012 | Hahn |
| 8,231,890 B2 | 7/2012 | Cruise et al. |
| 8,235,941 B2 | 8/2012 | Hayman et al. |
| 8,377,091 B2 | 2/2013 | Cruise et al. |
| 8,454,649 B2 | 6/2013 | Cragg et al. |
| 8,470,035 B2 | 6/2013 | Cruise et al. |
| 8,486,046 B2 | 7/2013 | Hayman et al. |
| 9,011,884 B2 | 4/2015 | Constant et al. |
| 9,114,200 B2 | 8/2015 | Constant et al. |
| 9,259,228 B2 | 2/2016 | Cruise et al. |
| 9,381,278 B2 | 7/2016 | Constant et al. |
| 9,451,963 B2 | 9/2016 | Cruise et al. |
| 9,456,823 B2 | 10/2016 | Constant et al. |
| 9,486,221 B2 | 11/2016 | Cruise et al. |
| 9,724,103 B2 | 8/2017 | Cruise et al. |
| 9,877,731 B2 | 1/2018 | Cruise et al. |
| 10,092,663 B2 | 10/2018 | Constant et al. |
| 10,124,090 B2 | 11/2018 | Constant et al. |
| 10,194,915 B2 | 2/2019 | Cruise et al. |
| 10,226,258 B2 | 3/2019 | Cruise et al. |
| 10,226,533 B2 | 3/2019 | Cruise et al. |
| 10,232,089 B2 | 3/2019 | Constant et al. |
| 10,499,925 B2 | 12/2019 | Cruise et al. |
| 10,639,396 B2 | 5/2020 | Baldwin |
| 10,946,100 B2 | 3/2021 | Cruise et al. |
| 11,160,557 B2 | 11/2021 | Cruise et al. |
| 11,179,492 B2 | 11/2021 | Baldwin et al. |
| 11,185,336 B2 | 11/2021 | Cruise et al. |
| 2001/0023325 A1 | 9/2001 | Ferrera |
| 2002/0026234 A1 | 2/2002 | Li et al. |
| 2002/0042378 A1 | 4/2002 | Reich et al. |
| 2002/0169473 A1 | 11/2002 | Sepetka et al. |
| 2002/0177855 A1 | 11/2002 | Greene, Jr. et al. |
| 2003/0014075 A1 | 1/2003 | Rosenbluth et al. |
| 2003/0021762 A1 | 1/2003 | Luthra et al. |
| 2003/0036582 A1 | 2/2003 | Yamakawa |
| 2003/0077272 A1 | 4/2003 | Pathak et al. |
| 2003/0078339 A1 | 4/2003 | Kiser et al. |
| 2003/0086874 A1 | 5/2003 | Whalen, II et al. |
| 2003/0100942 A1 | 5/2003 | Ken et al. |
| 2003/0134032 A1 | 7/2003 | Chaouk |
| 2003/0162863 A1 | 8/2003 | Satoh |
| 2003/0203991 A1 | 10/2003 | Schottman et al. |
| 2003/0211083 A1 | 11/2003 | Vogel et al. |
| 2003/0220245 A1 | 11/2003 | Hubbell et al. |
| 2003/0232198 A1 | 12/2003 | Lamberti et al. |
| 2003/0232895 A1 | 12/2003 | Omidian et al. |
| 2004/0006534 A1 | 1/2004 | Schaefer et al. |
| 2004/0024098 A1 | 2/2004 | Mather et al. |
| 2004/0059370 A1 | 3/2004 | Greene et al. |
| 2004/0091543 A1 | 5/2004 | Bell et al. |
| 2004/0097267 A1 | 5/2004 | Vallittu |
| 2004/0098028 A1 | 5/2004 | Martinez |
| 2004/0115164 A1 | 6/2004 | Pierce et al. |
| 2004/0158282 A1 | 8/2004 | Jones et al. |
| 2004/0209998 A1 | 10/2004 | De Vries |
| 2004/0242713 A1 | 12/2004 | Ghidoni |
| 2004/0247867 A1 | 12/2004 | Chaouk et al. |
| 2005/0003010 A1 | 1/2005 | Cohen et al. |
| 2005/0008610 A1 | 1/2005 | Schwarz et al. |
| 2005/0095428 A1 | 5/2005 | DiCarlo et al. |
| 2005/0106119 A1 | 5/2005 | Brandom et al. |
| 2005/0119687 A1 | 6/2005 | Dacey et al. |
| 2005/0124721 A1 | 6/2005 | Arthur et al. |
| 2005/0143484 A1 | 6/2005 | Fang et al. |
| 2005/0171572 A1 | 8/2005 | Martinez et al. |
| 2005/0175709 A1 | 8/2005 | Baty et al. |
| 2005/0196449 A1 | 9/2005 | DiCarlo et al. |
| 2005/0226935 A1 | 10/2005 | Kamath et al. |
| 2005/0281883 A1 | 12/2005 | Daniloff et al. |
| 2006/0052815 A1 | 3/2006 | Fitz et al. |
| 2006/0067883 A1 | 3/2006 | Krom et al. |
| 2006/0074370 A1 | 4/2006 | Zhou |
| 2006/0116713 A1 | 6/2006 | Sepetka et al. |
| 2006/0233854 A1 | 10/2006 | Seliktar et al. |
| 2006/0270750 A1 | 11/2006 | Almen et al. |
| 2007/0026039 A1 | 2/2007 | Drumheller et al. |
| 2007/0097627 A1 | 5/2007 | Taylor |
| 2007/0196454 A1 | 8/2007 | Stockman et al. |
| 2007/0202046 A1 | 8/2007 | Dave |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237720 A1 | 10/2007 | Padilla et al. |
| 2007/0237741 A1 | 10/2007 | Figuly et al. |
| 2007/0248567 A1 | 10/2007 | Pathak et al. |
| 2007/0254005 A1 | 11/2007 | Pathak et al. |
| 2007/0288084 A1 | 12/2007 | Lee et al. |
| 2008/0019921 A1 | 1/2008 | Zhang |
| 2008/0038354 A1 | 2/2008 | Stager et al. |
| 2008/0039890 A1 | 2/2008 | Matson et al. |
| 2008/0114277 A1 | 5/2008 | Ambrosio et al. |
| 2008/0208167 A1 | 8/2008 | Stankus |
| 2008/0226741 A1 | 9/2008 | Richard |
| 2008/0268250 A1 | 10/2008 | Hawkett |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0081275 A1 | 3/2009 | Rolfes et al. |
| 2009/0093550 A1 | 4/2009 | Rolfes et al. |
| 2009/0098510 A1 | 4/2009 | Zhang |
| 2009/0117033 A1 | 5/2009 | O'Gara |
| 2009/0155326 A1 | 6/2009 | Mack et al. |
| 2009/0181068 A1 | 7/2009 | Dunn |
| 2009/0221731 A1 | 9/2009 | Vetrecin et al. |
| 2009/0224438 A1 | 9/2009 | Stampfl |
| 2009/0232869 A1 | 9/2009 | Greene |
| 2009/0239962 A1 | 9/2009 | Dobashi |
| 2009/0258979 A1 | 10/2009 | Hawkett |
| 2009/0259302 A1 | 10/2009 | Trollsas et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0048750 A1 | 2/2010 | Blom |
| 2010/0086678 A1 | 4/2010 | Arthur et al. |
| 2010/0092533 A1 | 4/2010 | Stopek et al. |
| 2010/0241160 A1 | 9/2010 | Murphy |
| 2010/0247663 A1 | 9/2010 | Day et al. |
| 2010/0249913 A1 | 9/2010 | Dattaa et al. |
| 2010/0256777 A1 | 10/2010 | Dattta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0027172 A1 | 2/2011 | Wang et al. |
| 2011/0091549 A1 | 4/2011 | Blaskovich et al. |
| 2011/0182998 A1 | 7/2011 | Reb et al. |
| 2011/0184455 A1 | 7/2011 | Keeley |
| 2011/0190813 A1 | 8/2011 | Brownlee et al. |
| 2011/0202016 A1 | 8/2011 | Zugates et al. |
| 2012/0029101 A1 | 2/2012 | Senda |
| 2012/0041481 A1 | 2/2012 | Daniloff et al. |
| 2012/0083523 A1 | 4/2012 | Richard et al. |

(56) References Cited

U.S. PATENT DOCUMENTS

| | | |
|---|---|---|
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Bartling et al. |
| 2012/0238644 A1 | 9/2012 | Gong et al. |
| 2012/0244198 A1 | 9/2012 | Malmsjo et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0087736 A1 | 4/2013 | Baker |
| 2013/0108574 A1 | 5/2013 | Chevalier et al. |
| 2014/0056806 A1 | 2/2014 | Vemengo et al. |
| 2014/0274945 A1 | 9/2014 | Blaskovich et al. |
| 2014/0277057 A1 | 9/2014 | Ortega et al. |
| 2014/0329932 A1 | 11/2014 | Baker |
| 2022/0039802 A1 | 2/2022 | Cruise et al. |

FOREIGN PATENT DOCUMENTS

| | | |
|---|---|---|
| CN | 102107025 B | 5/2014 |
| EP | 809519 B1 | 12/1997 |
| EP | 1599258 B1 | 8/2008 |
| EP | 1601392 B1 | 4/2009 |
| WO | 1991/004732 A1 | 9/1990 |
| WO | 1991/016057 A | 10/1991 |
| WO | 1994/003155 A1 | 2/1994 |
| WO | 1997/022365 A1 | 6/1997 |
| WO | 1997/026939 A1 | 7/1997 |
| WO | 1997/027888 A1 | 8/1997 |
| WO | 1998/001421 A1 | 1/1998 |
| WO | 1998/043615 A1 | 10/1998 |
| WO | 1998/055103 A1 | 12/1998 |
| WO | 1999/023954 A1 | 5/1999 |
| WO | 1999/044538 A1 | 9/1999 |
| WO | 1999/056783 A1 | 11/1999 |
| WO | 1999/065401 A1 | 12/1999 |
| WO | 2000/027445 A1 | 5/2000 |
| WO | 2000/038651 A1 | 7/2000 |
| WO | 2000/074577 A1 | 12/2000 |
| WO | 2001/068720 A1 | 9/2001 |
| WO | 2002/005731 A1 | 1/2002 |
| WO | 2002/096302 A1 | 12/2002 |
| WO | 2003/043552 A1 | 5/2003 |
| WO | 2005/032337 A2 | 4/2005 |
| WO | 2007/016371 A2 | 2/2007 |
| WO | 2007/147145 A2 | 12/2007 |
| WO | 2000/078846 A1 | 12/2008 |
| WO | 2009/086208 A2 | 7/2009 |
| WO | 2010/033022 A1 | 3/2010 |
| WO | 2011/038291 A1 | 3/2011 |
| WO | 2011/053555 A1 | 5/2011 |
| WO | 2012/039602 A1 | 3/2012 |
| WO | 2012/101455 A1 | 8/2012 |
| WO | 2012/120138 A1 | 9/2012 |
| WO | 2012/145431 A3 | 10/2012 |
| WO | 2012/171478 A1 | 12/2012 |
| WO | 2013/158781 | 10/2013 |
| WO | 2015/153996 A1 | 10/2015 |
| WO | 2015/167751 A1 | 11/2015 |
| WO | 2015/167752 A1 | 11/2015 |
| WO | 2016/201250 A1 | 12/2016 |

OTHER PUBLICATIONS

Almany, Biomaterials, 26, 2005, 2467-2477, Biosynthetic hydrogel scaffolds made from fibrinogen and polyethylene glycol for 3D cell cultures.
Carelli V. et al., "Silicone microspheres for pH-controlled gastrointestinal drug delivery," 1999, International Journal of Pharmaceutics, V179, p. 73-83.
Chirila et al., Poly(2-hydroxyethyl metharcrylate) sponges ans implant materials: in vivo and in vitro evaluation of cellular invasion. Biomaterials, 14(1):26-38 (1993).
Constant et al., Preparation, Characterization, and Evaluation of Radiopaque Hydrogel Filaments for Endovascular Embolization. Journal of Biomedical Materials Research Part B: Applied Biomaterials, vol. 89B, No. 2, pp. 306-313 (2008).
Edleman et al., Controlled and modulated release of basic fibroblast growth factor. Biomaterials, vol. 12, pp. 619-626 (1991).
Elbert et al., Conjugate addition reactions combined with free-radical cross-linking for the design of materials for tissue engineering. Biomacromolecules, (2): 430-441 (2001).
European Search Opinion for EP Application No. 10819570 dated Mar. 31, 2014.
European Search Opinion for EP Application No. 10827370 dated Apr. 1, 2014.
Graves et al., Endovascular occlusion of the carotid or vertebral artery with temporary proximal flow arrest and nircocoils: clinical results. AJNR Am. J. Neuroradiol., vol. 18, pp. 1201-1206 (1997).
Hoekstra, D., Hyaluronan-modified surfaces for medical devices. Medical Device & Diagnostic Industry, pp. 48-56 (1999).
Hogg et al., Interaction of platelet-derived growth factor with thrombospondin 1. Biochem. J. 326, pp. 709-716 (1997).
Horak et al., Hydrogels in endovascular embolization. II. Clinical use of spherical particles. Biomaterials, 7(6): 467-470 (1986).
Horak et al., New radiopaque polyHEMA-based hydrogel particles. J. Biomed. Matter Res., 34(2): 183-188 (1997).
Huang, et al., "Synthesis and Characterization of Self-Assembling Block Copolymers Containing Adhesive Molecules," Polymer Preprints, vol. 42, No. 2, 2001, pp. 147-148.
International Search Report dated Dec. 17, 2010 for International Patent Application No. PCT/US2010/053972.
International Search Report dated Feb. 5, 2009 for International Patent Application No. PCT/US2007/071395.
International Search Report dated Aug. 14, 2013 for International PCT Application No. PCT/US2013/037007 filed on Apr. 17, 2013.
International Search Report and Written Opinion dated Jun. 29, 2015 for International Application No. PCT/US2015/024289 filed on Apr. 3, 2015.
International Search Report and Written Opinion dated Jun. 29, 2015 for International Application No. PCT/US2015/024290 filed on Apr. 3, 2015.
International Search Report and Written Opinion dated Jul. 14, 2015 for International Application No. PCT/US2015/024284 filed on Apr. 3, 2015.
Kim, Drug release from pH-sensitive interpenetrating polymer networks hydrogel based on poly (ethylene glycol) Macromer and Poly (acrylic acid) prepared by UV Cured Method, ArchPharmRes, vol. 19(1), 1996, p. 18-22.
Klier, Self Associating Networks of Poly(methacrylic acid g-ethylene glycol) Marcomolecules 1990, vol. 23, 1990, p. 4944-4949.
Larsen et al., Hylan gel composition for percutaneous embolization. Journal of Biomedical Materials Research, vol. 25, Issue 6, pp. 699-710 (1991).
Latchaw et al., Polyvinyl foam embolization of vascular and neoplastic lesions of the head, neck, and spine. Radiology, 131: 669-679 (1979).
Li, Jian et al., Preparation of PEG/Aac copolymerric hydrogel and study of pH-sensitivity. Chemistry World, Issue 1, pp. 20-23 (2005).
Mellott, Michael B. et al., Release of protein from highly cross-linked hydrogels of poly(ethylene glycol) diacrylate fabricated by UV polymerization. Biomaterials, 22(2001) 929-941.
Murayama et al., Cellular responses of bioabsorbable polymeric material and guglielmi detachable coil in experimental aneurysms. Stroke, pp. 1120-1128 (2002).
Persidis, A., Tissue engineering. Nature Biotechnology, 17, pp. 508-510 (1999).
Schmutz et al., Embolization of cerebral arteriovenous malformations with silk: histopathologic changes and hemorrhagic complications. AJNR Am. J. Neuroradiol., vol. 18, pp. 1233-1237 (1997).
Schoenmakers, The effect of the linker on the hydrolysis rate of drug-linked ester bonds, J. Cont. Rel., 95, 2004, pp. 291-300.
Supplementary European Search Report for EP Application No. 10819570 dated Mar. 31, 2014.

(56) References Cited

OTHER PUBLICATIONS

Supplementary European Search Report for EP Application No. 10827370 dated Apr. 1, 2014.
Vinuela et al., Guglielmi detachable coil embolization of acute intracranial aneurysm: perioperative anatomical and clinical outcome in 403 patients. J. Neurosurg., vol. 86, pp. 475-482 (1997).
Woerly et al., Intracerebral implantation of hydrogel-coupled adhesion peptides: tissue reaction. Journal of Neural Transplantation & Plasticity, vol. 5, No. 4, pp. 245-255 (1995).
Written Opinion dated Aug. 14, 2013 for International PCT Application No. PCT/US2013/037007 filed on Apr. 17, 2013.
Zollikofer et al., A combination of stainless steel coil and compressed ivalon: a new technique for embolization of larger arteries and arteriovenous fistulas. Radiology, 138:229-231 (1981).
Zollikofer et al., Therapeutic blockade of arteries using compressed invalon. Radiology, 136: 635-640 (1980).
Son et al., Preparation of properties of PEG-modified PHEMA hydrogel and the morphological effect. Macromolecular Research, vol. 14, No. 3, pp. 394-399 (2006).
International Search Report and Written Opinion dated Sep. 23, 2016 for International Application No. PCT/US2016/036924 filed on Jun. 10, 2016.
Supplementary European Search Report for EP Application No. 15785350 dated Nov. 13, 2017.
"Wavy line", Illustrated Glossary of Organic Chemistry, accessed at http://www.chem.ucla.edu/~harding/IGOC/W/wavy_line.html on Jul. 21, 2016.
Moysan et al., Gemcitabine versus modified gemcitabine: a review of several promising chemical modifications. HAL Archive inserm-00787112 (2013).
Polymer Products. Sigma-Aldrich (2019).

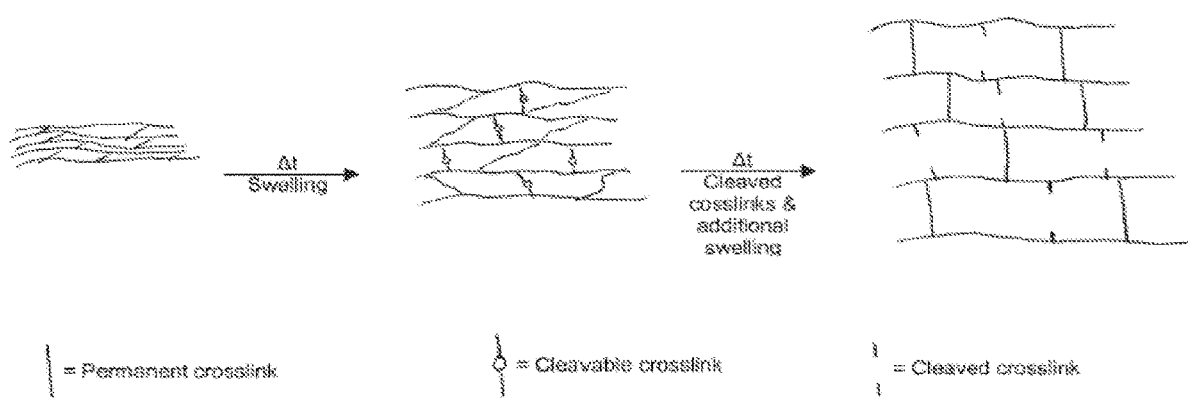
Scheme 2

POLYMERS

CROSS REFERENCE TO RELATED APPLICATIONS

This application is a continuation of U.S. patent application Ser. No. 16/838,730, filed Apr. 2, 2020, which is a divisional of U.S. patent application Ser. No. 15/179,212, filed Jun. 10, 2016, issued as U.S. Pat. No. 10,639,396 on May 5, 2020, which claims the benefit of U.S. provisional patent application No. 62/174,425, filed Jun. 11, 2015, the entire disclosure of each of which are incorporated herein by reference.

FIELD

The present invention relates generally to expansile polymers and medical treatment methods using the polymers.

SUMMARY

Described herein generally are expansile polymers such as hydrogels. The polymers can be formed as filaments. Methods of forming these polymers are also described. Further, medical treatment methods using the polymers are described. In some embodiments, when formed as a filament, the filaments described herein possess enough structural strength to not require support members. In other embodiments, the hydrogel filaments require support members. The filaments can also be opacified in order to visualize the filaments using medically relevant imaging techniques.

In one embodiment described herein are expansile devices for implantation in an animal, such as a mammal, such as a human. The expansile devices can comprise an expansile polymer including a reaction product of a polymerization solution including a macromer, a monomer, a first crosslinker, and a second crosslinker. In some embodiments, the second crosslinker is cleavable. In some embodiments, the second cleavable crosslinker imparts a secondary expansion to the expansile polymer.

The expansile devices can include at least one visualization element, which can be metallic powders, gadolinium, superparamagnetic iron oxide particles, barium sulfate, or a combination thereof. In one embodiment, the at least one visualization element is barium sulfate.

The monomer used in the herein described polymers can be pH sensitive and provide a first expansion to the expansile polymer. In other embodiments, the monomer may not be pH sensitive. In other embodiments, a monomer may not be used. In some embodiments, a macromer may be pH sensitive and/or provide expansion characteristics to the polymer. In some embodiments, the macromers and the monomers may have expansion characteristics.

In some embodiments, the first crosslinker can be N,N'-methylenebisacrylamide.

The second cleavable crosslinker can be an acrylate based crosslinker such as a methacrylate based crosslinker. In some embodiments, the second cleavable crosslinker can be an acrylic anhydride based crosslinker. The acrylic anhydride can be a methacrylate based anhydride crosslinker and can have a structure

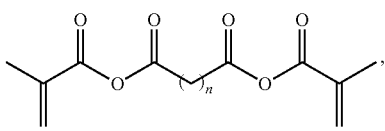

wherein n is 0, 1, 2, 3, 4, or 5. Further, the acrylic anhydride based crosslinker can be synthesized by reaction of a di-acid with methacrylic anhydride.

Methods of forming expansile polymers are also described. Methods can comprise polymerizing a polymer from a polymerization solution comprising a macromer, a monomer, a first crosslinker, and a second cleavable crosslinker. The methods can further include a step of treating said polymer in a non-physiological pH for a predetermined amount of time thereby creating an environmentally responsive hydrogel.

In some embodiments, the non-physiological pH that the polymers are treated in can be basic. In other embodiments, the non-physiological pH can be acidic.

BRIEF DESCRIPTION OF THE DRAWINGS

FIG. 1 depicts Scheme 2 showing a cleavable second type of crosslinker included in the hydrogel structure or matrix.

DETAILED DESCRIPTION

Described herein generally are expansile polymers such as hydrogels. The polymers can be formed into virtually any shape or form. In one embodiment, the polymers can be formed as filaments or other elongated structures. The polymers can have tuned rates of expansion and can incorporate a secondary expansion mechanism by including a crosslinker that can cleave upon a particular physiological event and allow expansion to what the polymer would normally expand to without the cleavable crosslinker. In other words, cleavable crosslinks can prevent full expansion or retard expansion until a cleavable event occurs and the polymer can fully expand.

Methods of forming the polymers are also described herein, including methods of making the polymers environmentally responsive and expandable at a predetermined rate for a predetermined amount of time. This expansion rate can be tailored using at least the secondary expansion mechanism by incorporation of a second cleavable crosslinker. Polymer expansion can be further tailored by including different types of cleavable crosslinkers such as a third, fourth, fifth or subsequent cleavable crosslinkers. In other embodiments, expansion can be tailored by using a different density or concentration of cleavable crosslinkers.

The expansile polymers and associated methods are for occluding structures and malformations resulting from one or more cerebral and/or peripheral vascular diseases. The polymers can have delayed and/or controlled rates of expansion. These controlled rates of expansion give surgeons a sufficient amount of time to deliver the polymer through a microcatheter or catheter filled with blood or saline at physiological pH without the need to rush as a result of immediate expansion. For use with a catheter, a polymer filament may be desired. Further, the polymers can include one or more visualization agents, for example, radiopaque elements or fillers to allow visualization during implantation.

Generally, the polymers, e.g., hydrogel filaments, can be deployed within the vasculature using standard practices and microcatheters/catheters to occlude blood flow.

As used herein, the term "environmentally responsive" refers to a material (e.g., a hydrogel or polymer described herein) that is sensitive to changes in environment including but not limited to pH, temperature, and pressure. Many of the expansile materials described herein are environmentally responsive at physiological conditions.

As used herein, the term "non-resorbable" refers to a material (e.g., a hydrogel) that cannot be readily and/or substantially degraded and/or absorbed by bodily tissues.

As used herein, the term "unexpanded" refers to the state at which a hydrogel is substantially not hydrated and, therefore, not expanded. In some embodiments described herein, a hydrogel filament is generally unexpanded prior to implantation into a patient.

As used herein, the term "ethylenically unsaturated" refers to a chemical entity (e.g., a macromer, monomer or polymer) containing at least one carbon-carbon double bond.

In some embodiments, when formed as a filament or other elongated structure, the filaments described herein may not have support members, such as no metal or metallic support members, to aid in supporting the filaments before, during and after implantation. When formed as a filament or other elongated structure, the filaments can possess enough structural column strength to not require support members.

The polymers described when provided as filaments or other elongated structures can have round, square, rectangular, triangular, pentagonal, hexagonal, heptagonal, octagonal, ellipsoidal, rhomboidal, torx, or star-shaped cross-sectional shapes. A filament can be described as having a three dimensional shape such as, but not limited to a thread, string, hair, cylinder, fiber, or the like. The filament can be elongated meaning that its length exceeds its width or diameter by at least 5, 10, 15, 20, 50, 100, 500, 1,000 or more times.

The filaments can be delivered through a catheter or microcatheter using a liquid flush (e.g. saline). The filaments have sufficient column strength to alleviate the need for a metal support member, yet soft and flexible enough to navigate through vasculature. However, in some embodiments, the filaments described herein do not have sufficient column strength to be advanced out of a catheter device by pushing with a metal wire. Here, as described above, a liquid flush, in some cases a pressurized liquid flush, can be used to advance the filaments through and out of a catheter or microcatheter.

The polymers described herein can be formed from polymerization solutions or prepolymer solutions comprising such components as one or more solvent(s), one or more macromer(s), one or more monomer(s), one or more crosslinker(s), one or more visualization agent(s), and one or more initiator(s). Some components are optional. In one embodiment, the hydrogel filaments can include a polymer which can be a reaction product of (i) one or more macromers, (ii) one or more monomers, and/or (iii) two or more different crosslinkers, wherein one of the crosslinkers is a cleavable crosslinker. The polymers can also optionally include one or more pharmaceutical agents. The polymers can also include one or more visualization agents.

A particular combination of monomers/macromers/crosslinkers can provide differing polymeric physical properties. Different polymeric physical properties can include, but are not limited to tensile strength, elasticity, and/or delivery through a microcatheter or catheter.

The solvent's function in the polymerization solution is complete dissolution of all macromers, monomers, crosslinkers, initiators, and/or soluble visualization agents needed to form a particular filament. In other embodiments, the solvent can dissolve substantially all of the macromers, monomers, cross-linkers, initiators, and/or soluble visualization agents needed to form a particular filament. In some embodiments, the visualization agent or agents do not dissolve in the solvent.

If a liquid monomer (e.g. 2-hydroxyethyl methacrylate) is used, a solvent may not be necessary. The solvent, if necessary, is selected based on the solubility of the components of the polymerization solution. Solvents can include isopropanol, ethanol, water, dichloromethane, and acetone. However, any number of solvents can be utilized and a skilled artisan can match a solvent to a particular polymer system.

Solvent concentrations can range from about 20% w/w to about 80% w/w of the polymerization solution. In other embodiments, the solvent ranges from about 40% w/w to about 60% w/w or about 30% w/w to about 50% w/w. In one embodiment, the solvent makes up about 40% w/w of the polymerization solution.

Macromers described herein can include large molecular weight compounds such as polymers having one or more reactive groups. In some embodiments, macromers with solubility in solvents and functional groups amenable to modifications may be used. Polyethers, due to their solubility in a variety of solvents, their availability in a variety of forms, and their available hydroxyl groups, may be used as macromers. Other macromers can include, but are not limited to, poly(ethylene glycol), poly(propylene glycol), and poly(tetramethylene oxide).

In other embodiments, a low molecular weight macromer can be used and/or in other embodiments, a branched macromer may be used. A low molecular weight, branched macromer can include at least three reactive moieties per molecule so that a high crosslink density of the finalized polymer can be achieved. Example low molecular weight, branched macromers can include ethoxylated pentaerythritol having four end groups per molecule, and ethoxylated trimethylolpropane having three end groups per molecule.

In still other embodiments, non-polyether polymers with functional groups available for modification, such as poly (vinyl alcohol), can also be used as macromers.

Macromers can be present at a concentration of about 10% w/w, about 15% w/w, about 20% w/w, about 25% w/w, about 30% w/w, about 35% w/w, about 40% w/w, about 45% w/w, about 50% w/w, at least about 10% w/w, between about 10% w/w and about 40% w/w, between about 15% w/w and about 25% w/w, between about 15% w/w and about 50% w/w, or between about 15% w/w and about 30% w/w, of the polymerization solution. In one embodiment, the macromer concentration is about 15% w/w of the polymerization solution.

The molecular weight of the macromer can alter the mechanical properties of the resulting polymer or hydrogel filament. In some embodiments, the alteration of the mechanical properties can be substantial. Smaller molecular weights result in polymers with sufficient column strength to be pushed through microcatheters and catheters when formed as a filament or other elongated structures. Larger molecular weights can result in polymer filaments that can be pushed through microcatheters and catheters with more difficulty. As such, the macromers described herein can have a molecular weight of about 50 g/mole, about 100 g/mole, about 200 g/mole, about 300 g/mole, about 400 g/mole, about 500 g/mole, about 1,000 g/mole, about 1,500 g/mole, about 2,000 g/mole, about 2,500 g/mole, about 3,000 g/mole, about 3,500 g/mole, about 4,000 g/mole, about 4,500 g/mole, about 5,000 g/mole, at least about 50 g/mole, at least about 100 g/mole, between about 50 g/mole and about 5,000 g/mole, between about 100 g/mole and about 5,000 g/mole, between about 1,000 g/mole and about 5,000 g/mole, between about 100 g/mole and about 1,000 g/mole, or between about 500 g/mole and about 1,000 g/mole. In one embodiment, the molecular weight is between about 500 g/mole to about 1,500 g/mole.

The polymerization solutions can include at least one macromer. The macromer can be of low molecular weight, shapeable, multifunctional (e.g. difunctional), ethylenically unsaturated or a combination thereof. At least one of the macromer's roles is to impart the desired mechanical properties and/or structural framework to the herein described polymers. In general, any polymer can function as a macromer. However, polymers with solubility in solvents and functional groups amenable to modifications can also be used. Polyethers, due to their solubility in a variety of solvents, their availability in a variety of forms, and their available hydroxyl groups, can be used. Poly(ethylene glycol), poly(propylene glycol), ethyoxylated trimethylol propane, and poly(tetramethylene oxide) can all be suitable for use herein. In another embodiment, a macromer can be poly(ethylene glycol). Poly(ethylene glycol) is preferred because of its solubility in aqueous solutions. Likewise, cross-linked networks of poly(ethylene glycol) swell in aqueous solutions. Non-polyether polymers with functional groups available for modification, such as poly(vinyl alcohol), can also be utilized as macromers. Macromer concentrations can range from about 5% w/w to about 50% w/w, about 10% w/w to about 40% w/w, about 15% w/w to about 30% w/w, or about 16% w/w to about 29% w/w of the polymerization solution. In one embodiment, the macromer concentration is about 19% w/w, about 25% w/w or about 29% w/w of the polymerization solution.

In some embodiments, the macromer is shapeable. Shapeability describes the macromer's relative rigidity and its ability to hold a particular shape. For example, a shapeable macromer according to the present description can be formed using a device such as a mandrel and can hold the resulting shape for implantation.

The molecular weight of the macromer can dramatically change the resulting polymer's mechanical properties. Smaller molecular weights result in polymers when formed as filaments that have sufficient column strength to be pushed through microcatheters and catheters. Larger molecular weights result in polymers that when formed as filaments, can require more effort to be pushed through microcatheters and catheters.

The macromers described herein have a molecular weight ranging from about 100 g/mole to about 100,000 g/mole or about 500 g/mole to about 50,000 g/mole. In one embodiment, molecular weight ranges from about 5,000 g/mole to about 15,000 g/mole. In another embodiment, the molecular weight is about 10,000 g/mole. One embodiment includes poly(ethylene glycol) diacrylamide with a molecular weight of about 10,000 g/mole.

Any functional groups associated with the macromers described can be derivatized. The functional groups of the macromers can be derivatized to impart ethylenically unsaturated moieties allowing free radical polymerization of the hydrogel. Functionalities for free radical polymerization can include acrylates, methacrylates, acrylamides, vinyl groups, and derivatives thereof. Alternatively, other reactive chemistries can be employed to polymerize the hydrogel, for example, nucleophile/N-hydroxysuccinimde esters, nucleophile/halide, vinyl sulfone or maleimide. In one embodiment, a functional group of the macromer is an acrylate.

Biostability (or non restorability) or biodegradation can be imparted to polymers described by altering the synthetic route to derivatize macromer functional groups. If biostability is desired, linkage stability in the physiological environment can be utilized. In one embodiment, a biostable linkage is an amide. The macromer hydroxyl group(s) is converted to an amino group followed by reaction with acryloyl chloride to form an acrylamide group. If biodegradation is desired, linkages susceptible to breakage in a physiological environment can be utilized. In some embodiments, biodegradable linkages can include esters, polyesters, and amino acid sequences degradable by enzymes.

Monomers used to form the herein described polymers can have low molecular weights and/or can contain a single polymerizable group. If present, the monomer(s) can aid in polymerization and impart specific mechanical properties to the resulting polymer. The monomers can be any molecule with a single functionality and conducive to a desired mechanical property.

Specific monomers can include, but are not limited to, t-butyl acrylamide, 2-hydroxyethyl methacrylate, hydroxyl propyl acrylate, hydroxyl butylacrylate, and derivatives thereof. The hydrophobicity and bulky structure of these specific monomers can impart column strength to the resulting polymer.

In some embodiments, a visualization agent can be a monomer and incorporated into the polymeric structure.

Monomers, if present, can be present at a concentration of about 5% w/w, about 10% w/w, about 15% w/w, about 20% w/w, about 25% w/w, about 30% w/w, about 35% w/w, about 40% w/w, about 45% w/w, about 50% w/w, at least about 5% w/w, between about 5% w/w and about 40% w/w, between about 10% w/w and about 50% w/w, between about 5% w/w and about 30% w/w, or between about 5% w/w and about 20% w/w, of the prepolymer solution.

Monomers sensitive to pH can be utilized in the polymers described herein thereby imparting environmental sensitivity to them. The main function of the pH sensitive monomer is to permit control over the polymers rate of expansion. Such monomers must include functionality allowing incorporation into the resulting polymer during polymerization and ionizable moieties, for example, carboxylic acids or amines. Concentrations of pH sensitive monomers in the polymerization solution can range from about 1% to about 12.5%. In some embodiments, pH sensitive monomers can be acrylic acid, methacrylic acid, amino methacrylate, amino methacrylamide, and derivatives and salts thereof. In some embodiments, pH sensitive monomers are not utilized.

Generally, the controlled rate of expansion of the polymers is imparted through the incorporation of ethylenically unsaturated monomers with ionizable functional groups, (e.g. acidic or basic groups). For example, if acrylic acid is incorporated into the cross-linked polymeric network, it can be introduced through a microcatheter filled with blood or saline at physiological pH. The polymer cannot and may not expand until the carboxylic acid groups deprotonate. Conversely, if a basic, amine containing monomer is incorporated into the cross-linked network, the polymer can be introduced through a microcatheter filled with blood or saline at physiological pH. The polymer cannot and will not fully expand until the amine groups are protonated.

In one embodiment, pH-sensitive monomers are incorporated into the polymers to control the rate of expansion to permit delivery through microcatheters and catheters filled with physiological fluids. In one embodiment, ethylenically unsaturated carboxylic acids are incorporated into the polymers. In another embodiment, salts of ethylenically unsaturated carboxylic acids are incorporated into the polymers and subsequently the polymers are incubated in a low pH solution to protonate all the salts of the carboxylic acids. Expansion occurs in a physiological environment as the carboxylic acids deprotonate. In another embodiment, salts of ethylenically unsaturated amines are incorporated into the polymers and subsequently the polymers are incubated in a high pH solution to deprotonate the salts of the amines. Expansion occurs in a physiological environment as the amines protonate. In yet another environment, pH sensitive monomers are not incorporated into the polymers.

Non-pH sensitive monomers can also be used to aid in polymerization of the polymers and impart specific mechanical properties to the polymers. The non-pH sensitive monomers can be any molecule with a single functionality to incorporate into the polymers and/or a structure conducive to the desired mechanical property. The non-pH sensitive monomers can be, for example, hydrophobic thereby imparting column strength to the polymers. Also or in addition, the non-pH sensitive polymers can have a bulky structure further imparting column strength. Internal hydrogen bonding within the non-pH sensitive monomer imparts increasing tensile strength. In some embodiments, non-pH sensitive monomers can be t-butyl acrylamide, 2-hydroxyethyl methacrylate, and derivatives thereof. Concentrations of non-pH sensitive monomers can range from about 0% to about 20% w/w, about 15% w/w, about 12% w/w or about 11% w/w of the polymerization solution.

In one embodiment, depending on the monomers chosen for a particular polymer, significant fluid uptake by the polymer can occur and a large increase in the volume of the polymer can occur in a physiological environment. In another embodiment, monomers chosen allow only a small amount of fluid uptake by the polymer and only a small increase in the volume of the polymer occurs in a physiological environment. In yet another environment, monomers chosen prevent fluid uptake by the polymer and the volume of the polymer remains unchanged in a physiological environment.

Crosslinkers can also be utilized to impart cross-linking of the resulting polymer. A crosslinker can be any molecule with at least two functionalities to incorporate into the resulting polymer. The crosslinker can also be a structure conducive to the desired mechanical property imparted on the finalized polymer.

Crosslinkers can include an ester, a carbonate, a thioester, an anhydride, or a combination thereof. In other embodiments, multiples of each of an ester, a carbonate, anhydrides, and/or a thioester can be included. In one embodiment, a crosslinker can be an anhydride.

Other crosslinkers can include N,N-methylenebisacrylamide and ethylene glycol dimethacrylate.

Cross-linker(s), when used in the described polymers, impart desired mechanical properties. The cross-linker can be any molecule with at least two functionalities to incorporate into the polymers and preferably a structure conducive to the desired mechanical property. In one embodiment, a cross-linker is N,N-methylenebisacrylamide. Concentrations of the cross-linker can be less than about 1% w/w, less than about 0.8% w/w, less than about 0.5% w/w, or less than about 0.1% w/w of the polymerization solution. In one embodiment, the concentration of cross-linker is about 1% w/w.

A second type of crosslinker can also be included in the final polymer. The second type of crosslinker can impart a secondary mechanism of expansion to the hydrogel filaments. This secondary mechanism can be one that increases the swelling size of the hydrogel, but does not impact the initial rate of swelling. In some embodiments, the second type of crosslinker can retard full expansion of the polymer until the crosslinker is cleaved.

Possibilities for a second type of crosslinker can include crosslinkers that can be cleaved or degraded. For example, cleavable linkages include esters, polyesters, and amino acid sequences degradable by enzymes. In other embodiments, the second type of crosslinker can include hydrolyzable moieties such as anhydrides. Anhydrides will begin to cleave as the hydrogel hydrates. However, in some embodiments, the cleavage rate may be slower than that of the initial expansion of the hydrogel resulting from hydration.

Cleavable crosslinkers can include acrylate based crosslinkers such as acrylic anhydride based crosslinkers. These crosslinkers can be synthesized by reaction of a di-acid with methacrylic anhydride. An example synthetic scheme (Scheme 1) is

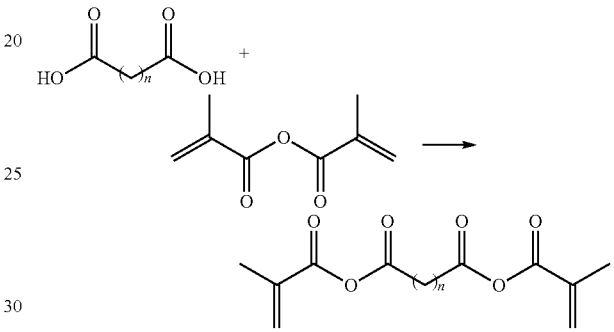

Scheme 1 wherein n is 0, 1, 2, 3, 4, or 5.

In some embodiments, the di-acid crosslinker can include ethylene, ethylene glycol, or propylene glycol repeating units to modulate the water solubility and the rate of degradation.

In some embodiments, when an anhydride based crosslinker is used, a resulting polymer can be sensitive to water. Thus, in some embodiments, gelation and purification of the resulting polymer can be performed in the absence of water.

In one embodiment, a first type of crosslinker and a second type of crosslinker can be used in the herein described hydrogels and polymers. In one embodiment, the second crosslinker can be a cleavable crosslinker. For example, as illustrated FIG. 1 in Scheme 2, a cleavable second type of crosslinker is included in the hydrogel structure or matrix.

The second type of crosslinker can incorporate secondary covalent cleavable crosslinks, in addition to a first type of permanent crosslinks, into the backbone. As these secondary covalent cleavable crosslinks are broken the polymer or hydrogel can expand to a larger diameter than the hydrogel would expand without the secondary crosslinkers present. In other words, hydrogels incorporating a second cleavable crosslinker in addition to a first permanent crosslinker can have a first expanded diameter when the hydrogel is swollen and a second, larger diameter when the cleavable crosslinks are broken or cleaved.

In effect, the hydrogel can initially expand to the extents limited by the initial crosslink density imparted by the cleavable crosslinks (e.g., the first diameter), and then subsequent hydrolysis of the cleavable crosslinks can allow the hydrogel to expand to a greater size (e.g., the second diameter).

In further embodiments, a third, fourth, fifth or more different cleavable crosslinkers can be included in a polymer or hydrogel described. Each cleavable crosslinker can have a different length and different degradation time to allow multiple steps of expansion before a final expansion size is achieved.

In some embodiments, the concentration of the second, cleavable type of crosslinker can be about 5% w/w, about 4% w/w, about 3% w/w, about 2% w/w, about 1% w/w, about 0.5% w/w between about 5% w/w and about 1% w/w, between about 2% w/w and about 0.5% w/w, or between about 5% w/w and about 0.5% w/w of the polymerization solution.

The concentration of all the crosslinkers in a polymerization solution can be less than about 10% w/w, less than about 5% w/w, less than about 4% w/w, less than about 3% w/w, less than about 2% w/w, less than about 1% w/w, or less than about 0.5% w/w of the polymerization solution.

In one embodiment, polymerization of the herein described polymers can be initiated using an initiator. An initiator can be azobisisobutyronitrile (AIBN) or a water soluble AIBN derivative. Other initiators useful according to the present description include N,N,N',N'-tetramethylethylenediamine, ammonium persulfate, benzoyl peroxides, 2,2'-azobis(2-methylpropionamidine)dihydrochloride, and combinations thereof, including azobisisobutyronitriles. The polymerization solution can be polymerized by reduction-oxidation, radiation, heat, or any other method known in the art. Radiation cross-linking of the polymerization solution can be achieved with ultraviolet light or visible light with suitable initiators or ionizing radiation (for example, electron beam or gamma ray) without initiators. Cross-linking can be achieved by application of heat, either by conventionally heating the solution using a heat source such as a heating well, or by application of infrared light to the polymerization solution.

When used in the polymerization solutions described herein, an initiator starts the polymerization of the polymerization solution components. An exemplary initiator includes 2,2'-azobis(2-methylpropionamidine)dihydrochloride. Concentrations of the initiator can be less than about 1% w/w or less than about 0.5% w/w of the polymerization solution.

Visualization agents can also be added to the polymers described herein since metallic support members may not be used in conjunction with the presently described polymers. Generally, in the art, metallic support members aid in the visualization of embolic devices. Here, this may not be the case. The visualization agents impart visibility of the resulting polymers when imaged using a medically relevant imaging technique such as fluoroscopy, computed tomography, or magnetic resonance techniques.

Visualization of the polymers under fluoroscopy can be imparted by the incorporation of solid particles of radiopaque materials such as barium, bismuth, tantalum, platinum, gold, and other heavy nuclei species into the polymers or by the incorporation of iodine molecules polymerized into the polymer structure. In one embodiment, a visualization agent for fluoroscopy can be barium sulfate. Visualization of the polymers under computed tomography imaging can be imparted by incorporation of solid particles of barium or bismuth. Metals visible under fluoroscopy generally result in beam hardening artifacts that preclude the usefulness of computed tomography imaging for medical purposes. In one embodiment, a visualization agent for fluoroscopy can be barium sulfate. Concentrations of barium sulfate rendering the hydrogel filaments visible using fluoroscopic and computed tomography imaging can range from about 30% w/w to about 60% w/w, about 35% w/w to about 50% w/w, or about 39% w/w to about 47% w/w of the polymerization solution.

Visualization of the polymers under magnetic resonance imaging can be imparted by the incorporation of solid particles of superparamagnetic iron oxide or gadolinium molecules polymerized into the polymer structure. In one embodiment, a visualization agent for magnetic resonance is superparamagnetic iron oxide with a particle size of 10 microns. Concentrations of superparamagnetic iron oxide particles to render the polymers visible using magnetic resonance imaging can range from about 0.01% w/w to about 1% w/w, about 0.05% w/w to about 0.5% w/w, or about 0.1% w/w to about 0.6% w/w of the polymerization solution.

In one embodiment, a polymer can be formed from a reaction product of a difunctional, low molecular weight, ethylenically unsaturated, shapeable macromer, an ethylenically unsaturated monomer, a visualization element, a cross-linker, a second cleavable crosslinker that retards expansion of the polymer, and an initiator.

In another embodiment, a polymer can include a difunctional, low molecular weight, ethylenically unsaturated, shapeable macromer, an ethylenically unsaturated monomer, a visualization element, a cross-linker, and a second cleavable crosslinker that retards expansion of the polymer.

The polymers can have many characteristic properties one of which is bending resistance. The polymers when formed as filaments or other elongated structures can generally have a dry bending resistance of about 20 mg to about 200 mg, about 20 mg to about 32 mg or about 100 mg to about 200 mg. In the wet state, the bending resistance lowers drastically to about 2 mg to about 50 mg, about 2 mg to about 5 mg, or about 25 mg to about 50 mg.

Another characteristic is average ultimate tensile strength of the polymers when formed as filaments or other elongated structures. The filaments described herein have an average ultimate tensile strength of about 0.18 lbf to about 0.65 lbf, about 0.18 lbf to about 0.25 lbf, or about 0.52 lbf to about 0.65 lbf.

Methods of preparing the polymers is also described. The polymerization solution is prepared by dissolving the macromer, pH sensitive monomers, non-pH sensitive monomers, cross-linker, cleavable crosslinker, initiator, and soluble visualization agents in the solvent. After dissolution of these components, an insoluble visualization agent can be suspended in the polymerization solution. Mixing of the polymerization solution containing an insoluble visualization agent with a homogenizer aids in suspension of the insoluble visualization agent. The polymerization solution can then be polymerized to provide a polymer. The polymer can be dried.

In some embodiments, to form a filament, before polymerization, the polymerization solution can be injected into tubing with an inner diameter ranging from about 0.001 inches to about 0.075 inches and incubated for several hours in boiling water, for example, at 100° C., and subsequently overnight at 80° C. to complete the polymerization. The immersion in boiling water allows for rapid heat transfer from the water to the polymerization solution contained in the tubing. The selection of the tubing imparts microcatheter or catheter compatibility. For delivery through microcatheters, tubing diameters can range from about 0.006 inches to about 0.025 inches. For delivery through 4 and 5 Fr catheters, tubing can have diameters from about 0.026 inches to about 0.045 inches. In one embodiment, the tubing is made from HYTREL® (DuPont, Wilmington, Del.). The HYTREL® tubing can be dissolved in solvents, facilitating removal of the formed polymer from the tubing.

If a filament as described herein is wrapped around a mandrel prior to polymerization of the polymerization solution, the resulting polymer will maintain the shape of the filament around the mandrel or at least retain a memory of the shape. Using this technique, helical, tornado, and complex shapes can be imparted to the hydrogel filament. When the tubing is wrapped around a mandrel, trapezoidal and/or oval tubing can be used. After wrapping around the mandrel, the oval shape of the tubing is rounded and the resulting filament has a round shape.

If HYTREL® tubing is utilized, the filament can be recovered by incubating the tubing in a solution of 25% w/w phenol in chloroform followed by washing in chloroform and ethanol. After the filament has been washed, it is dried, and a dried hydrogel filament is produced. The length of a dried filament can range from about 0.01 cm to about 1,000 cm, about 0.1 cm to about 500 cm, about 0.25 cm to about 250 cm, or about 0.5 cm to about 100 cm. The diameter of a filament can range from about 0.01 inches to about 0.1 inches, about 0.001 inches to about 0.01 inches, or about 0.006 inches to about 0.075 inches. In one embodiment the filament has a diameter less than about 0.05 inches, 0.04 inches, or 0.031 inches.

In some embodiments, the polymer described herein can expand initially, before second crosslinker cleavage to about 5%, about 10%, about 20%, about 30%, about 40%, about 50%, at most about 50%, at most about 40%, or between about 10% and about 50% of the polymers full expansion diameter. Then, after cleavage of the second crosslinker, the polymer described herein can expand to about 50%, about 60%, about 70%, about 80%, about 90%, 100%, at least about 50%, at least about 60%, or between about 50% and 100% of the polymers full expansion diameter.

In some embodiments, the polymers described can be incubated in a low pH or high pH solution to protonate or depronate the pH sensitive monomer incorporated into the polymer as necessary rendering it environmentally responsive. The environmentally responsive polymer can expand to a particular dimension after being subjected to a particular pH environment. However, the cleavable crosslinker can prevent the polymer from expanding to its full expansion parameters until the cleavable crosslinkers have been broken and the polymer is allowed to folly expand.

In some embodiments, the second cleavable crosslinker can add about 60 sec, about 1 min, about 5 min, about 10 min, about 15, min, about 20 min, at least about 1 min, at least about 5 min, or at least about 15 min of time before the polymer is fully expanded.

Example 1

Implantation of a Polymer Filament with a Secondary Expansion Mechanism

A patient is implanted with a polymer filament which is crosslinked with a non-degradable crosslinker and a cleavable crosslinker and a pH sensitive monomer. The polymer filament had been treated in an acidic pH solution and dried to render the filament environmentally responsive.

The filament is delivered through a microcatheter to a vessel occlusion. The filament expands in response to the change in pH. After about 10 min, the filament is 50% expanded. After about 15 min, the filament is about 60% expanded. At about 20 min, the cleavable crosslinking bonds begin to break and after 25 min, the filament is about 95% expanded.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. An expansile polymer, including a reaction product of a polymerization solution including a macromer, a monomer, a first crosslinker, and a second cleavable crosslinker,
wherein the expansile polymer has a dry bending resistance to wet bending resistance ratio of about 200:50 to about 20:2, a dry bending resistance of about 20 mg to about 200 mg, and a wet bending resistance of about 2 mg to about 50 mg.

2. The expansile polymer of claim 1, wherein the expansile polymer has a full expansion size that includes a primary expansion and a secondary expansion, wherein the secondary expansion is retarded by the second cleavable crosslinker.

3. The expansile polymer of claim 1, further including at least one visualization element.

4. The expansile polymer according to claim 3, wherein the at least one visualization element is selected from metallic powders, gadolinium, superparamagnetic iron oxide particles, barium sulfate, or a combination thereof.

5. The expansile polymer according to claim 3, wherein the at least one visualization element is barium sulfate.

6. The expansile polymer according to claim 1, wherein the monomer is pH sensitive and provides the primary expansion to the expansile polymer.

7. The expansile polymer according to claim 1, wherein the second cleavable crosslinker is an acrylate based crosslinker.

8. The expansile polymer according to claim 7, wherein the acrylate based crosslinker is an acrylic anhydride based crosslinker.

9. The expansile polymer according to claim 8, wherein the acrylic anhydride based crosslinker has a structure

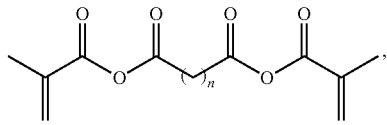

wherein n is 0, 1, 2, 3, 4, or 5.

10. The expansile polymer according to claim 8, wherein the acrylic based anhydride crosslinker is synthesized by reaction of a di-acid with methacrylic anhydride.

11. A filament, comprising an expansile polymer, including a reaction product of a polymerization solution including a macromer, a monomer, a first crosslinker, and a second cleavable crosslinker,
wherein the expansile polymer has a dry bending resistance to wet bending resistance ratio of about 200:50 to about 20:2, a dry bending resistance of about 20 mg to about 200 mg and a wet bending resistance of about 2 mg to about 50 mg.

12. The filament of claim 11, wherein the filament includes no support members.

13. The filament of claim 11, wherein the expansile polymer has a full expansion size that includes a primary expansion and a secondary expansion, wherein the secondary expansion is retarded by the second cleavable crosslinker.

14. The filament of claim 11, further including at least one visualization element.

15. The filament of claim 14, wherein the at least one visualization element is selected from metallic powders, gadolinium, superparamagnetic iron oxide particles, barium sulfate, or a combination thereof.

16. The filament of claim 14, wherein the at least one visualization element is barium sulfate.

17. The filament of claim 11, wherein the monomer is pH sensitive and provides the primary expansion to the expansile polymer.

18. The filament of claim 11, wherein the second cleavable crosslinker is an acrylate based crosslinker.

19. The filament of claim 18, wherein the acrylate based crosslinker is an acrylic anhydride based crosslinker.

20. The filament of claim 19, wherein the acrylic anhydride based crosslinker has a structure

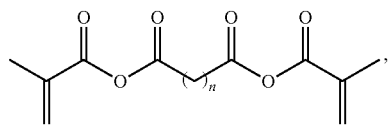

wherein n is 0, 1, 2, 3, 4, or 5.

21. The filament of claim 19, wherein the acrylic based anhydride crosslinker is synthesized by reaction of a di-acid with methacrylic anhydride.

* * * * *